United States Patent [19]

Cullen et al.

[11] 4,021,551

[45] May 3, 1977

[54] 3,6-BIS-(HETEROCYCLIC AMINOACYL-AMINO)-ACRIDINES AND SALTS THEREOF

[75] Inventors: Ernest Cullen, Montreal, Canada; Peter Meindl, Vienna, Austria; Hans Tuppy, Vienna, Austria; Gerhard Bodo, Vienna, Austria

[73] Assignee: Boehringer Ingelheim GmbH, Ingelheim am Rhein, Germany

[22] Filed: July 30, 1975

[21] Appl. No.: 600,434

Related U.S. Application Data

[63] Continuation-in-part of Ser. No. 366,732, June 4, 1973, Pat. No. 3,907,804.

[30] Foreign Application Priority Data

June 7, 1972 Austria .............................. 4878/72

[52] U.S. Cl. .......................... 424/246; 260/243 B; 260/247.2 A; 260/268 TR; 260/279 R; 424/248.54; 424/250; 424/257

[51] Int. Cl.² ............ C07D 401/12; C07D 417/12; C07D 413/12; A61K 31/54

[58] Field of Search .... 260/279 R, 243 B, 247.2 A, 260/268 H, 268 TR; 424/257, 246 CA, 248, 250

[56] References Cited

UNITED STATES PATENTS 1,889,704  11/1932  Schuleman et al. ............ 260/279 A
3,318,896  5/1967  Pribyl et al. ...................... 260/287

OTHER PUBLICATIONS

Canonico et al., Chemical Abstracts, vol. 69, 96,327k (1968).

Adhya et al., Chemical Abstracts, vol. 75, 48,640j (1971).

Mueller et al., Chemical Abstracts, vol. 79, 78,575s (1973).

Primary Examiner—Richard J. Gallagher
Assistant Examiner—Diana G. Rivers
Attorney, Agent, or Firm—Hammond & Littell

[57] ABSTRACT

Compounds of the formula

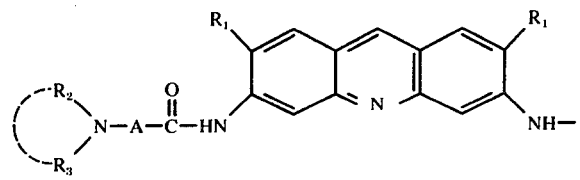

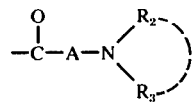

wherein
$R_1$ is hydrogen or methyl,
$R_2$ and $R_3$, together with each other and the nitrogen atom to which they are attached, form a saturated or unsaturated heterocyclic ring system which may optionally contain one or more additional heteroatoms, and
A is lower alkylene or aryl-lower alkylene, and non-toxic, pharmacologically acceptable acid addition salts thereof; the compounds as well as their salts are useful as inducers of the formation of interferon.

4 Claims, No Drawings

3,6-BIS-(HETEROCYCLIC AMINOACYL-AMINO)-ACRIDINES AND SALTS THEREOF

This is a continuation-in-part of copending application Ser. No. 366,732 filed June 4, 1973, now U.S. Pat. No. 3,907,804 granted Sept. 23, 1975.

This invention relates to novel 3,6-bis-(heterocyclic aminoacyl-amino)-acridines and their acid addition salts, as well as to methods of preparing these compounds.

More particularly, the present invention relates to a novel class of 3,6-bis-(heterocyclic aminoacyl-amino)-acridines represented by the formula

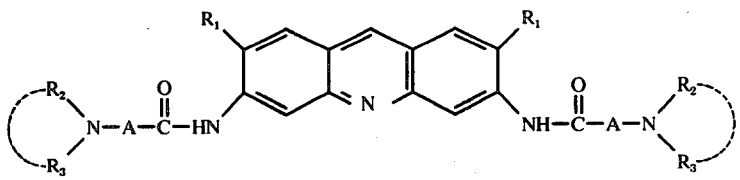

(I)

wherein
$R_1$ is hydrogen or methyl,
$R_2$ and $R_3$, together with each other and nitrogen atom to which they are attached, form a saturated or unsaturated heterocyclic ring system which may optionally contain one or more additional heteroatoms, and
A is lower alkylene or aryl-lower alkylene, and non-toxic, pharmacologically acceptable acid addition salts thereof.

The compounds embraced by formula I may be prepared either by reacting a 3,6-bis-(haloacyl-amino)-acridine of the formula

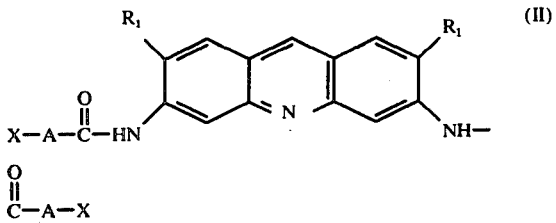

(II)

wherein $R_1$ and A have the same meanings as in formula I and X is chlorine, bromine or iodine, with a heterocyclic amine of the formula

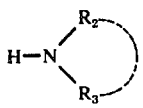

(III)

wherein $R_2$ and $R_3$ have the same meanings as in formula I; or by reacting a 3,6-diamino-acridine of the formula

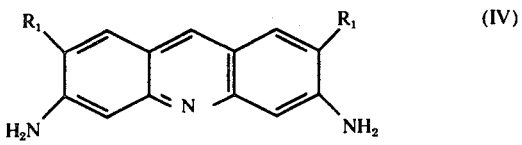

(IV)

wherein $R_1$ has the meanings previously defined, with a heterocyclic aminoester of the formula

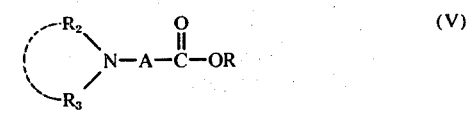

(V)

wherein $R_2$, $R_3$ and A have the meanings previously defined and R is lower alkyl.

In either case, the reaction is carried out at room temperature or elevated temperatures, optionally in the presence of an inert solvent medium and, if required, in the presence of an inorganic or organic base, such as sodium bicarbonate, potassium carbonate, sodium hydroxide, triethylamine or the like. Examples of suitable solvent media are ethanol, dimethylformamide, dimethylsulfoxide or the like, or mixture of these; if the amine of the formula III is itself a liquid at the reaction temperature, the presence of a separate solvent medium is not essential, provided that a sufficient excess of the liquid amine is present to act as the solvent medium.

The starting compounds embraced by formula II may be prepared by known methods, such as by acylation of a corresponding acridine derivative with free amino-substituents of the formula IV under conventional acylation conditions, such as by reaction with an acyl halide or an acyl anhydride, preferably while heating.

The compounds of the formula I are organic bases and therefore form acid addition salts with inorganic or organic acids. Examples of non-toxic, pharmacologically acceptable acid addition salts are those formed with hydrohalic acids, nitric acid, sulfuric acid, orthophosphoric acid, oxalic acid, citric acid, tartaric acid, fumaric acid, maleic acid, propionic acid, butyric acid, acetic acid, methanesulfonic acid, succinic acid, 8-chlorotheophylline or the like.

Using the above-described methods, the following compounds can be prepared:
3,6-bis-(pyrrolidino-acetylamino)-acridine,
3,6-bis-[2-(piperidino)-propionylamino]-acridine,
3,6-bis-[(3'-methylpiperidino)-acetylamino]-acridine,
3,6-bis-[(2'-methylpiperidino)-acetylamino]-acridine,
3,6-bis-[(4'-methylpiperidino)-acetylamino]-acridine,
3,6-bis-[(3'-hydroxypiperidino)-acetylamino]-acridine,
3,6-bis-[(4'-ethoxycarbonylpiperidino)-acetylamino]-acridine,
3,6-[(4'-hydroxymethylpiperidino)-acetylamino]-acridine,
3,6-bis-(1,2,5,6-tetrahydropyridino-acetylamino)-acridine,
3,6-bis-(hexamethyleneimino-acetylamino)-acridine,
3,6-bis-[(4'-β-hydroxyethyl-piperazino)-acetylamino]-acridine,
3,6-bis-(morpholino-acetylamino)-acridine,
3,6-bis-[(N-thiomorpholino)-acetylamino]-acridine,
3,6-bis-[(N-thiomorpholino-S-oxide)-acetylamino]-acridine, 3,6-bis-[(N-thiomorpholino-S,S-dioxide)-acetylamino]-acridine,
3,6-bis-(piperidino-acetylamino)-acridine, and their non-toxic, pharmacologically acceptable acid addition salts.

The following examples further illustrate the present invention and will enable others skilled in the art to understand it more completely. It should be understood, however, that the invention is not limited solely to the particular examples given below.

EXAMPLE 1

3,6-Bis-(morpholinoacetyl-amino)-acridine trihydrochloride dihydrate

A mixture consisting of 35 gm of 3,6-bis-(chloroacetyl-amino)-acridine, 35 gm of morpholine and 600 ml of dimethylformamide was heated for 2 hours on a boiling water bath. Thereafter, the unreacted morpholine and the solvent were evaporated, and the residue was purified by repeated crystallization from acetic acid/water, ethanol/water and aqueous ethanol containing a trace of hydrochloric acid, yielding 15 gm of the compound of the formula

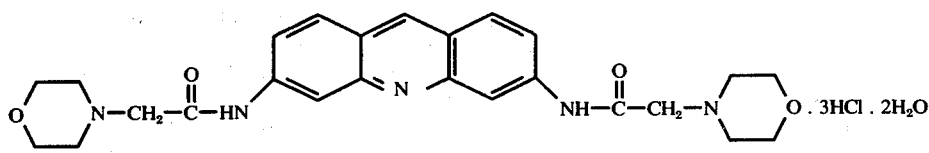

which had a melting point of 300° C.

The starting compound, 3,6-bis-(chloroacetylamino)-acridine, was prepared in conventional manner by acetylating proflavine with chloroacetyl chloride or chloroacetic accid anhydride.

EXAMPLE 2

3,6-Bis-(piperidinoacetyl-amino)-acridine 9.4 ml (0.11 mol) of piperidine were added to a solution of 4.0 gm (0.011 mol) of 3,6-bis-(chloroacetylamino)-acridine in dimethylformamide, and the mixture was heated at 100° C for about 4 hours. Thereafter, the reaction mixture was allowed to cool and was then admixed with 22 ml of ethyl acetate. The piperidine hydrochloride which separated out slowly was separated by vacuum filtration. The clear filtrate was admixed with ethereal hydrochloric acid until the mixture reacted strongly acidic, and the precipitate formed thereby was collected by vacuum filtration, washed with an ample amount of ether and dried. The substance thus obtained was dissolved in 750 ml of water, and the resulting solution was admixed dropwise with 50 ml of aqueous 25% ammonia, accompanied by vigorous stirring. A brownish oil separated out which generally crystallized throughout, and the crystallizate was collected, thoroughly washed with water and dried at room temperature in vacuo over phosphorus pentoxide, yielding 4.94 gm (97.3% of theory) of raw 3,6-bis-(piperidinoacetyl-amino)-acridine of the formula

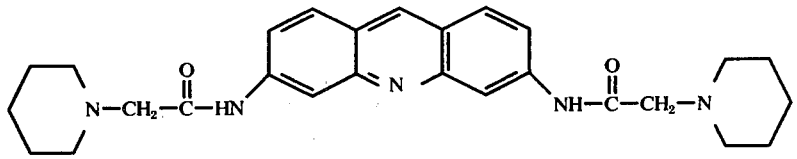

The raw product was recrystallized twice from ethanol, yielding 82% of theory of the pure product which had a melting point of 192°–194° C.

EXAMPLE 3

Using a procedure analogous to that described in Example 2, 91% of theory of 3,6-bis-[(pyrrolidino-acetyl)-amino]-acridine, m.p. 191°–193° C (recrystallized from ethanol/water), of the formula

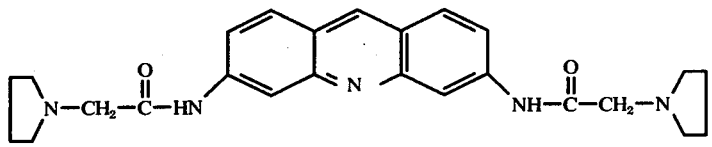

was obtained from 3,6-bis-(chloracetyl-amino)-acridine and pyrrolidine.

EXAMPLE 4

3,6-Bis-[(thiomorpholino-S-oxide-acetyl)-amino]-acridine hemihydrate

A solution of 5.0 gm (0.013 mol) of 3,6-bis-(chloroacetyl-amino)-acridine in 25 ml of dimethylformamide was admixed with 8.7 gm of thiomorpholine-S-oxide, and the mixture was heated for 4 hours at 100° C and then allowed to stand overnight at room temperature. The crystals formed thereby were collected by vacuum filtration, washed with ethyl acetate, dissolved in 250 ml of hot dioxane, and the solution was admixed with 500 ml of dilute ammonia, whereby an amorphous precipitate was formed which gradually crystallized throughout. Careful concentration of the solution to about 400 ml in vacuo at 60° C accelerated crystallization. 68% of theory of the compound of the formula

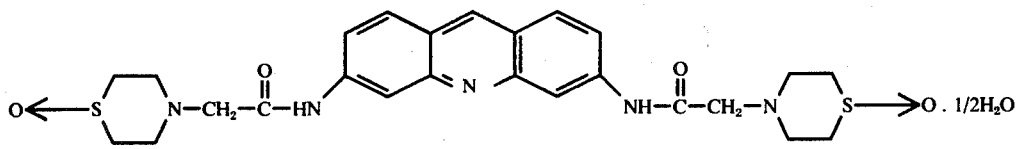

with a melting point of 177°–179° C was obtained.

EXAMPLE 5

Using a procedure analogous to that described in Example 4, 73% of theory of 3,6-bis-[(thiomorpholino-acetyl)-amino]-acridine hemihydrate, m.p. 140°–150° C (recrystallized from dioxane/ethanol/dilute ammonia), was obtained from 3,6-bis-(chloroacetyl-amino)-acridine and thiomorpholine.

EXAMPLE 6

Using a procedure analogous to that described in Example 4, 83% of theory of 3,6-bis-[(thiomorpholino-S,S-dioxide-acetyl)-amino]-acridine hydrate, m.p. 190°–192° C (recrystallized from dioxane/ethanol/dilute ammonia), was obtained from 3,6-bis-(chloroacetyl-amino)-acridine and thiomorpholine-S,S-dioxide.

EXAMPLE 7

3,6-Bis-[3'-methylpiperidino-acetyl)-amino]-acridine hemihydrate

A mixture consisting of 4.0 gm(0.011 mol) of 3,6-bis-(chloroacetyl-amino)-acridine, 4.0 gm (0.04 mol) of 3-methyl-piperidine and 25 ml of dimethylformamide was heated for 3 hours at 60° C. Thereafter, the clear reaction solution was introduced into 200 ml of dilute aqueous ammonia, accompanied by vigorous stirring, and the yellow precipitate formed thereby was collected by vacuum filtration, washed with water, dried in vacuo over phosphorus pentoxide at room temperature, and recrystallized first from 40 ml of hot ethanol and then from 150 ml of water. 71% of theory of the compound of the formula

EXAMPLE 8

Using a procedure analogous to that described in Example 7, 75% of theory of 3,6-bis-[2'-methyl-piperidino-acetyl)-amino]-acridine hemihydrate, m.p. 128°–130° C (recrystallized from ethanol/dilute ammonia), was obtained from 3,6-bis-(chloroacetyl-amino)-acridine and 2-methyl-piperidine.

EXAMPLE 9

Using a procedure analogous to that described in Example 7, 68% of theory of 3,6-bis-[(4'-methyl-piperidino-acetyl)-amino]-acridine hemihydrate, m.p. 218°–222° C (recrystallized from ethanol/dioxane/dilute ammonia), was obtained from 3,6-bis-(chloroacetyl-amino)-acridine and 4-methylpiperidine.

EXAMPLE 10

Using a procedure analogous to that described in Example 7, 84% of theory of 3,6-bis-[(4'-ethoxycarbonylpiperidino-acetyl)-amino]-acridine hemihydrate, m.p. 178°–182° C (recrystallized from methanol/dilute ammonia), of the formula

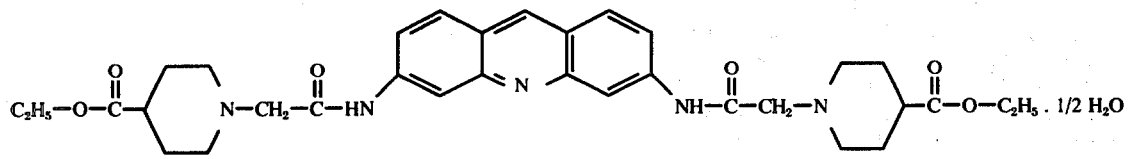

was obtained from 3,6-bis-(chloroacetyl-amino)-acridine and 4-ethoxycarbonyl-piperidine.

EXAMPLE 11

Using a procedure analogous to that described in Example 7, 71% of theory of 3,6-bis-[(1',2',5',6'-tetrahydropyridino-acetyl)-amino]-acridine hemihydrate, m.p. 95°–100° C (recrystallized from ethanol/water), was obtained from 3,6-bis-(chloroacetyl-amino)-acridine and 1,2,5,6-tetrahydropryidine.

EXAMPLE 12

Using a procedure analogous to that described in Example 7, 49% of theory of 3,6-bis-[N'-β-hydroxyethylpiperazino-acetyl)-amino]-acridine dihydrate, m.p. 228°–233° C (recrystallized from ethanol), of the formula

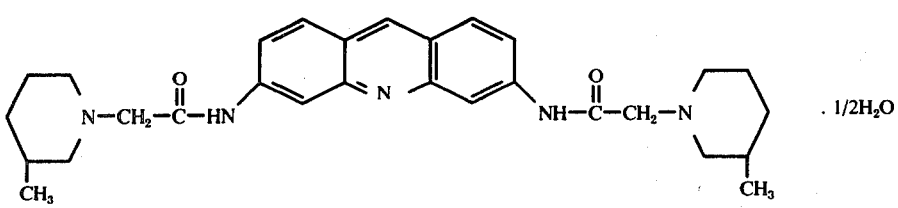

with a melting point of 97°–102° C was obtained.

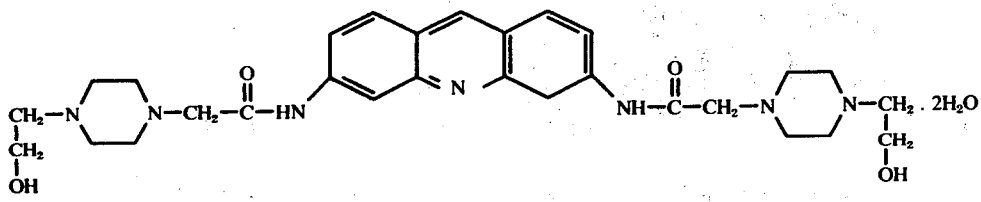

was obtained from 3,6-bis-(chloroacetyl-amino)-acridine and 4-β-hydroxyethyl-piperazine.

EXAMPLE 13

Using a procedure analogous to that described in Example 7, 75% of theory of 3,6-bis-[(hexamethyleneimino-acetyl)-amino]-acridine, m.p. 190°–193° C (recrystallized from ethanol/water), was obtained from 3,6-bis-(chloroacetylamino)-acridine and hexamethyleneimine.

EXAMPLE 14

Using a procedure analogous to that described in Example 7, 71% of theory of 3,6-bis-[(4'-hydroxymethylpiperidino-acetyl)-amino]-acridine .1½ H$_2$O, m.p. 145°– 150° C (recrystallized from methanol/water), was obtained from 3,6-bis-(chloroacetyl-amino)-acridine and 4-hydroxymethyl-piperidine.

EXAMPLE 15

Using a procedure analogous to that described in Example 7, 49% of theory of 3,6-bis-[(N'-methylpiperazinoacetyl)-amino]-acridine hemihydrate, m.p. 232°–235° C (recrystallized from water), was obtained from 3,6-bis-(chloroacetyl-amino)-acridine and N-methyl-piperazine.

EXAMPLE 16

3,6-Bis-[(3'-hydroxypiperidino-acetyl)-amino]-acridine hemihydrate

A solution of 4.0 gm (0.011 mol) of 3,6-bis-(chloroacetyl-amino)-acridine in 25 ml of dimethylformamide was admixed with 40 gm (0.039 mol) of 3-hydroxypiperidine, and the mixture was heated for three hours at 80° C. After the reaction had gone to completion, the reaction mixture was concentrated to about 10 ml by evaporation in vacuo, and then 200 ml of acetone as well as 40 ml of ethereal hydrochloric acid were added. The yellow precipitate formed thereby was collected by vacuum filtration, washed with water, dried and dissolved in 150 ml of hot water. While stirring the aqueous solution, 30 ml of aqueous 25% ammonia were added, and the precipitate formed thereby was collected and crystallized first from 20 ml of ethanol and then from 50 ml of dilute ammonia, yielding 86% of theory of the compound of the formula

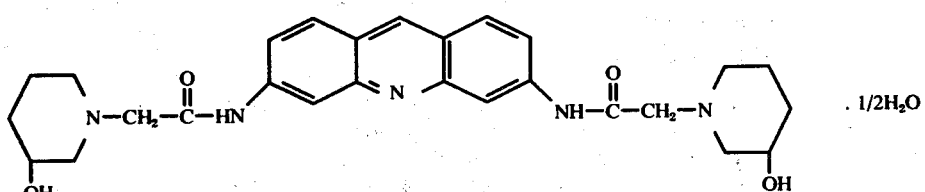

which had a melting point of 128°–130° C.

EXAMPLE 17

Using a procedure to that described in Example 16, 70% of theory of 3,6-bis[(4'-hydroxypiperidino-acetyl)amino]-acridine hydrate, m.p. 232°–235° C, was obtained from 3,6-bis-(chloroacetyl-amino)-acridine and 4-hydroxy-piperidine.

EXAMPLE 18

3,6-Bis-[α(2'-methylpiperidino)-propionyl-amino]-acridine hemihydrate

A mixture consisting of 6.0 gm of 3,6-bis(α-chloropropionyl-amino)-acridine, 15.2 gm of 2-methylpiperidine and 50 ml of dimethylformamide was heated for 5 hours at 100° C. Thereafter, the reaction mixture was concentrated by evaporation in vacuo to a small volume, admixed with 150 ml of ethyl acetate, and the 2-methylpiperidine hydrochloride precipitated thereby was separated by filtration. The filtrate was evaporated, the residue was dissolved in 100 ml of ethanol at 80° C, and the solution was admixed with about 60 ml of water until it started to turn cloudy. The precipitate formed thereby was collected and recrystallized from 70 ml of ethanol and 30 ml of water, yielding 6.55 gm (82% of theory) of the compound of the formula

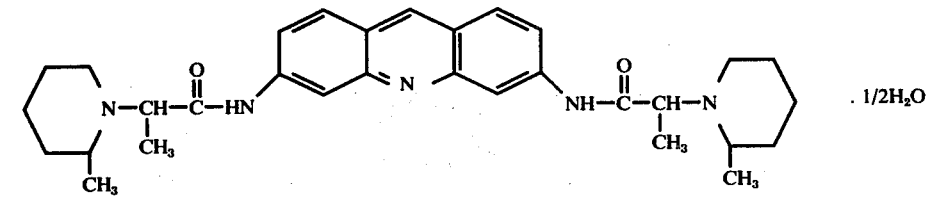

which had a melting point of 135°–143° C.

EXAMPLE 19

Using a procedure analogous to that described in Example 18, 68% of theory of 3,6-bis-[α-(piperidino)-propionyl-amino]-acridine hydrate, m.p. 197°–201° C (recrystallized from ethanol), was obtained from 3,6-bis-(α-chloropropionyl-amino)-acridine and piperidine.

EXAMPLE 20

Using a procedure analogous to that described in Example 8, 58% of theory of 3,6-bis-[α-(3'-methyl-piperidino)-propionyl-amino]-acridine hydrate, m.p. 160°–164° C (recrystallized from ethanol), was obtained from 3,6-bis-(α-chloropropionyl-amino)-acridine and 3-methyl-piperidine.

EXAMPLE 21

Using a procedure analogous to that described in Example 18, 56% of theory of 3,6-bis-[α-(4'-methyl-piperidino)-propionyl-amino]-acridine hydrate, m.p. 182°–186° C (recrystallized from ethanol/water), was obtained from 3,6-bis-(α-chloropropionyl-amino)-acridine and 4-methyl-piperidine.

EXAMPLE 22

Using a procedure analogous to that described in Example 18, 58% of theory of 3,6-bis-[α-(1',2',5',6'-tetrahydropyridino)-propionyl-amino]-acridine hemihydrate, an amorphous powder (precipitated from dilute hydrochloric acid with aqueous ammonia), was obtained from 3,6-bis-(α-chloropropionyl-amino)-acridine and 1,2,5,6-tetrahydropryridine.

EXAMPLE 23

3,6-Bis-[α-(hexamethyleneimino)-butyryl-amino]-acridine

A solution of 6.0 gm of 3,6-bis-(α-bromobutyryl-amino)-acridine in 20 ml of dimethylformamide was admixed with 11.7 gm of hexamethyleneimine, and the mixture was allowed to stand for 5 hours at 70° C. Thereafer, the reaction mixture was poured into 600 ml of water, and the precipitated solids were collected by high-vacuum filtration, dissolved in 200 ml of hot ethanol, the solution was admixed with 120 ml of water, and the mixture was allowed to stand in a refrigerator. The crystalline substance which separated out was collected, yielding 5.27 gm (82% of theory) of the compound of the formula

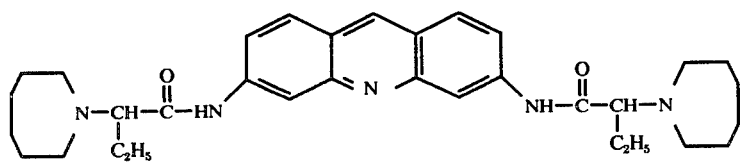

which had a melting point of 116°–118° C.

EXAMPLE 24

Using a procedure analogous to that described in Example 23, 78% of theory of 3,6-bis-[(α-piperidino-butyryl)-amino]-acridine hemihydrate, m.p. 103°–106° C (recrystallized from ethanol/water), was obtained from 3,6-bis-(α-chlorobutyryl-amino)-acridine and piperidine.

EXAMPLE 25

Using a procedure analogous to that described in Example 23, 80% of theory of 3,6-bis-[α-(2'-methyl-piperidino)-butyryl-amino]-acridine hemihydrate, m.p. 122°–124° C (recrystallized from ethanol/water), was obtained from 3,6-bis-(α-chlorobutyryl-amino)-acridine and 2-methyl-piperidine.

EXAMPLE 26

Using a procedure analogous to that described in Example 23, 82% of theory of 3,6-bis-[α-(3'-methyl-piperidino)-butyryl-amino]-acridine hydrate, m.p. 120°–125° C (recrystallized from ethanol/water), was obtained from 3,6-bis-(α-chlorobutyryl-amino)-acridine and 3-methyl-piperidine.

EXAMPLE 27

Using a procedure analogous to that described in Example 23, 58% of theory of 3,6-bis-[α-(4'-methyl-piperidino9-butyryl-amino]-acridine hemihydrate, m.p. 105°–108° C (recrystallized from ethanol/water), was obtained from 3,6-bis-(α-chlorobutyryl-amino)-acridine and 4-methyl-piperidine.

EXAMPLE 28

Using a procedure analogous to that described in Example 23, 60% of theory of 3,6-bis-[α-(1',2',5',6'-tetrahydropyridino)-butyryl-amino]-acridine hemihydrate, an amorphous powder (precipitated from dilute hydrochloric acid with aqueous ammonia), was obtained from 3,6-bis-(α-chlorobutyryl-amino)-acridine and 1,2,5,6-tetrahydropyridine.

EXAMPLE 29

Using a procedure analogous to that described in Example 23, 82.2% of theory of 3,6-bis-[(α-hexamethyleneimino-butyryl)-amino]-acridine, m.p. 116°–118° C (recrystallized from ethanol/water), was obtained from 3,6-bis-(α-chlorobutyryl-amino)-acridine and hexamethyleneimine.

EXAMPLE 30

3,6-Bis-[(α-1',2',5',6'-tetrahydropyridino-isobutyryl)-amino]-acridine . 1½ H$_2$O 9.8 gm of 1,2,5,6-tetrahydro-pyridine were added to a solution of 6.0 gm of 3,6-bis(α-bromo-isobutyrylamino)-acridine in 30 ml of dimethylformamide, and the mixture was allowed to stand for 5 hours at 70° C. Thereafter, the reaction solution was allowed to stand and was allowed to cool and was then stirred into 600 ml of water. The precipitate formed thereby was collected, dissolved in 100 ml of 1 N hydrochloric acid, and the resulting solution was first diluted with 50 ml of water and then admixed with 100 ml of 1 N ammonia. The precipitate formed thereby was collected and recrystallized first from 200 ml of ethanol and then from 100 ml of water, yielding 5.0 gm (82% of theory) of the compound of the formula

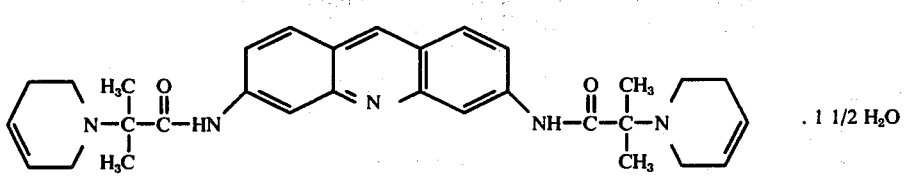

. 1 1/2 H₂O which had a melting point of 117°–122° C.

EXAMPLE 31

Using a procedure analogous to that described in Example 30, 70.9% of theory of 3,6-bis-[(α-piperidino-isobutyryl)-amino]-acridine trihydrate, m.p. 131°–137° C (recrystallized from ethanol), was obtained from 3,6-bis-(α-chloroisobutyryl-amino)-acridine and piperidine.

EXAMPLE 32

Using a procedure analogous to that described in Example 30, 64% of theory of 3,6-bis-[(α-hexamethyleneimino-isobutyryl)-amino]-acridine . 2.5 H₂O, m.p. 100°–102° C (recrystallized from ethanol/water, was obtained from 3,6-bis-(α-chloroisobutyryl-amino)-acridine and hexamethyleneimine.

EXAMPLE 33

Using a procedure analogous to that described in Example 30, 55.5% of theory of 3,6-bis-[(α-2′-methyl-piperidino-isobutyryl)-amino]-acridine, m.p. 125°–128° C (recrystallized from ethanol/water), was obtained from 3,6-bis-(α-chloroisobutyryl-amino)-acridine and 2-methyl-piperidine.

EXAMPLE 34

Using a procedure analogous to that described in Example 30, 60% of theory of 3,6-bis-[(α-3′-methyl-piperidino-isobutyryl)-amino]-acridine, m.p. 107°–110° C (recrystallized from ethanol/water), was obtained from 3,6-bis-(α-chloroisobutyryl-amino)-acridine and 3-methyl-piperidine.

EXAMPLE 35

Using a procedure analogous to that described in Example 30, 52% of theory of 3,6-bis-[(α-4′-methyl-piperidino-isobutyryl)-amino]-acridine, m.p. 133°–135° C (recrystallized from ethanol/water), was obtained from 3,6-bis-(α-chloroisobutyryl-amino)-acridine and 4-methyl-piperidine. those embraced by formula I above and their non-toxic, pharmacologically acceptable acid addition salts, have useful pharmacodynamic properties. More particularly, the compounds of the instant invention induce or stimulate the formation and release of interferon in vitro, as well as in vivo in warm-blooded animals, such as mice.

Particularly effective in this respect are those compounds of the formula I wherein $R_1$ is hydrogen, $R_2$ and $R_3$, together with each other and the nitrogen atom, are piperidino, and A is lower alkylene.

Interferon is a protein formed during the interaction of animal cells with viruses, which is capable of conferring on fresh animal cells of the same species a long-lasting resistance to infection with a wide range of viruses. In other words, the activity of an interferon is non-specific with respect to viruses, but specific with respect to the particular animal species.

In the absence of direct prophylactic or therapeutic methods for effectively combatting various virus infections, pharmacologists have long searched for compounds which are capable of significantly stimulating the formation of interferon. Although a number of compounds have been suggested for this purpose, such as living or killed viruses, endotoxin, phytohemagglutinin, trachoma and double-strand complexes of polyinosinic acid and polycyctidylic acid, the utility of these substances for the treatment of virus infections is significantly restricted due to serious drawbacks, such as low activity.

The effectiveness of the compounds of the present invention to stimulate the formation of interferon is illustrated by the following tests:

The test compound was administered perorally, with the aid of an esophageal sound, to a group of 3 to 5 SPF-strain laboratory mice of about 20 gm body weight. For this purpose the test compound was either dissolved in water or aqueous 20% acetic acid, or, in case of an insoluble compound, suspended in these vehicles after addition of 0.4% of methylcellulose. The dosage levels were 250 and 50 mgm/kg. 24 hours after administration of the test compound, the thorax of the animals was opened, the blood was withdrawn by heart puncture, the blood from all the animals was pooled, and the serum was prepared.

The serum thus obtained was investigated for interferon content in a tissue culture. For this purpose, monolayer-cultures of tissue cells from mice of the L-929 lineage were incubated for 24 hours with the serum sample under investigation. Each serum was tested in five different stages of dilution, and the test for each stage of dilution was repeated three times. Thereafter, the cultures were infested with vesicular stomatitis virus, and the virus propagation was determined 48 hours later by dyeing the cell turf with gentiana violet and counting the plaques which had formed.

The values thus obtained were plotted on a graph of dilution vs. number of plaques, and the degree of dilution which produced a 50% inhibition in the number of plaques formed in comparison to a serum obtained from untreated controls was graphically determined and was considered, by definition, to contain one biological unit. In order to be able to compare different tests with each other, a mouse interferon standard was always tested at the same time, and deviations, if any, from the theoretical value were corrected accordingly.

The following table shows the results obtained for a representative compound of the present invention, namely A = 3,6-bis-[(piperidino-acetyl)-amino]-acridine.

| Compound | Dose mgm/kg | Biological Units / ml serum |
|----------|-------------|------------------------------|
| A        | 50          | 83                           |
|          | 250         | 690                          |

Serum of untreated controls: 0 to maximum 6 units/ml. Thus, by virtue of their interferon production inducing activity, the compounds of the present invention are useful and effective for combatting a wide variety of virus infections in warm-blooded animals. In addition to vesicular stomatitis virus, the compounds of the invention will also effectively combat other viruses, such as arbor viruses, picona viruses, herpes virus, pox viruses, myxoviruses and the like.

Since interferon is, to a certain extent, also known to be effectively against non-viral pathogens, such as Chlamydia and protozoa (for example, the cause of psittacosis, the TRIC-agent, *toxoplasma gondii* and *plasmodium berghei*), the interferon production inducers of the present invention are also believed to be useful for combatting non-viral infections and non-viral benign tumors.

For pharmaceutical purposes the compounds according to the present invention are administered to warm-blooded animals perorally or parenterally as active ingredients in customary dosage unit compositions, that is, compositions in dosage unit form consisting essentially of an inert pharmaceutical carrier and one effective dosage unit of the active ingredient, such as tablets, coated pills, capsules, wafers, powders, solutions, suspensions, emulsions, syrups, suppositories and the like. One effective interferon-producing dosage unit of the compounds according to the present invention is from 1.66 to 16.7 mgm/kg body weight, preferably 4.15 to 8.3 mgm/kg body weight.

The following examples illustrate a few pharmaceutical dosage unit compositions comprising a compound of the present invention as an active ingredient and represent the best modes contemplated of putting the invention into practical use. The parts are parts by weight unless otherwise specified.

EXAMPLE 36

Coated pills

The pill core composition is compounded from the following ingredients:

| | |
|---|---|
| 3,6-Bis-[(piperidino-acetyl)-amino]-acridine | 500.0 parts |
| Lactose | 200.0 parts |
| Corn starch | 80.0 parts |
| Gelatin | 12.0 parts |
| Magnesium stearate | 8.0 parts |
| Total | 800.0 parts |

Preparation

The acridine compound, the lactose and the corn starch are intimately admixed with each other, the mixture is moistened with an aqueous 10% solution of the gelatin, the moist mass is granulated through a 1 mm-mesh screen, and the granulate is dried at 40° C, again passed through the screen and admixed with the magnesium stearate. The composition is then compressed into 800 mgm-pill cores which are subsequently coated with a thin shell consisting essentially of a mixture of sugar, titaniumdioxide, talcum and gum arabic, and finally polished with beeswax. Each coated pill contains 500 mgm of the acridine compound and is an oral dosage unit composition with effective interferon production inducing action.

EXAMPLE 37

Tablets

The tablet composition is compounded from the following ingredients:

| | |
|---|---|
| 3,6-Bis-[(piperidino-acetyl)-amino] | 500.0 parts |
| Lactose | 200.0 parts |
| Corn starch | 130.0 parts |
| Soluble starch | 12.0 parts |
| Magnesium stearate | 8.0 parts |
| Total | 850.0 parts |

Preparation

The acridine compound and the magnesium stearate are intimately admixed with each other, the mixture is granulated with an aqueous solution of the soluble starch, the granulate is dried and thoroughly admixed with the lactose and the corn starch, and the resulting composition is compressed into 850 mgm-tablets in a conventional tablet making machine. Each tablet contains 500 mgm of the acridine compound and is an oral dosage unit composition with effective interferon production inducing action.

EXAMPLE 38

Capsules

The capsule filler composition is compounded from the following ingredients:

| | |
|---|---|
| 3,6-Bis-[(piperidino-acetyl)-amino]-acridine | 500.0 parts |
| Gelatin | 2.0 parts |
| Total | 502.0 parts |

Preparation

The acridine compound and the gelatin are admixed with each other, the mixture is granulated with an aqueous solution of gelatin, the granulate is dried, and 502 mgm-portions of the dry granulate are filled into gelatin capsules of suitable size. Each capsule contains 500 mgm of the acridine compound and is an oral dosage unit composition with effective interferon production inducing action.

EXAMPLE 39

Solution

The solution is compounded from the following ingredients:

| | |
|---|---|
| 3,6-Bis-[(piperidino-acetyl)-amino]-acridine | 25.0 parts |
| Sodium hydrogen phosphate . 2H$_2$O | 0.25 parts |
| Disodium hydrogen phosphate | 4.50 parts |
| Methyl p-hydroxy-benzoate | 0.17 parts |
| Propyl p-hydroxy-benzoate | 0.07 parts |
| Sorbitol | 180.00 parts |
| Saccharin sodium | 5.00 parts |
| Flavoring | 0.25 parts |
| Ethanol | 50.00 parts |
| Distilled water q.s.ad | 500.00 parts |
| | by vol. |

Preparation

The sodium hydrogen phosphate, the disodium hydrogen phosphate, the saccharin sodium, the sorbitol and the acridine compound are dissolved in about 300 parts by volume of distilled water (solution I).

The two p-hydroxy-benzoates and the flavoring are dissolved in the ethanol (solution II).

Solution I is admixed with solution II, and the mixed solution is diluted with distilled water to 500 parts by volume.

Each 5 ml of the solution contain 250 mgm of the acridine compound and are an oral dosage unit composition with effective interferon production inducing action.

Analogous results are obtained when any one of the other acridine derivatives embraced by formula I or a non-toxic, pharmacologically acceptable acid addition salt thereof is substituted for the particular acridine compound in Examples 36 through 39. Likewise, the amount of active ingredient in these illustrative examples may be varied to achieve the dosage unit range set forth above, and the amounts and nature of the inert pharmaceutical carrier ingredients may be varied to meet particular requirements.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. A compound of the formula

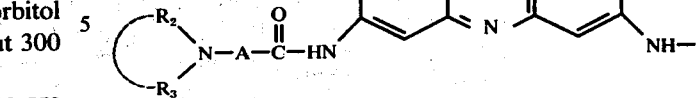

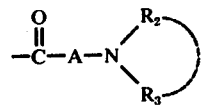

wherein $R_1$ is hydrogen or methyl, $R_2$ and $R_3$, together with each other and the nitrogen atom to which they are attached, are pyrrolidino, piperidino, methyl-piperidino, hydroxy-piperidino, hydroxymethyl-piperidino, ethoxycarbonyl-piperidino, tetrahydropyridino, hexamethylenimino, N'-methyl-piperazino, N'-β-hydroxyethyl-piperazino, morpholino, thiomorpholino, S-oxide-thiomorpholino or S,S-dioxido-thiomorpholino, and A is lower alkylene, or a non-toxic, pharmacologically acceptable acid addition salt thereof.

2. A compound of claim 1, which is 3,6-bis-(piperidinoacetyl-amino)-acridine or a non-toxic, pharmacologically acceptable acid addition salt thereof.

3. A pharmaceutical dosage unit composition consisting essentially of an inert pharmaceutical carrier and an effective interferon production-inducing amount of a compound of claim 1.

4. The method of stimulating the production of interferon in a warm-blooded animal, which comprises administering to said animal an effective interferon production-inducing amount of a compound of claim 1.

* * * * *

UNITED STATES PATENT OFFICE
CERTIFICATE OF CORRECTION

Patent No. 4,021,551           Dated May 3, 1977

Inventor(s) ERNEST CULLEN, PETER MEINDL, HANS TUPPY and GERHARD BODO

It is certified that error appears in the above-identified patent and that said Letters Patent are hereby corrected as shown below:

Column 6, line 51  -  After "3,6-bis-[" insert -- ( --

" 9, " 7  -  "Example 8" should read -- Example 18 --

" 10, " 17  -  "9" should be deleted

" 11, " 49  -  After "piperidine." insert -- The compounds of the present invention, that is, --

" 13, " 46  -  After "3,6-bis-[" insert -- ( --

Signed and Sealed this second Day of August 1977

[SEAL]

Attest:

RUTH C. MASON  
*Attesting Officer*

C. MARSHALL DANN  
*Commissioner of Patents and Trademarks*